United States Patent
Durst et al.

(10) Patent No.: US 12,331,360 B2
(45) Date of Patent: Jun. 17, 2025

(54) RISK DETERMINATION FOR NEOPLASIA AND CANCER

(71) Applicant: oncgnostics GmbH, Jena (DE)

(72) Inventors: Matthias Durst, Jena (DE); Ingo B. Runnebaum, Jena (DE); Martina Schmitz, Jena (DE); Alfred Hansel, Jena (DE)

(73) Assignee: Oncgnostics GmbH, Jena (DE)

( * ) Notice: Subject to any disclaimer, the term of this patent is extended or adjusted under 35 U.S.C. 154(b) by 0 days.

(21) Appl. No.: 16/650,849

(22) PCT Filed: Sep. 29, 2017

(86) PCT No.: PCT/EP2017/074829
§ 371 (c)(1),
(2) Date: Mar. 25, 2020

(87) PCT Pub. No.: WO2019/063097
PCT Pub. Date: Apr. 4, 2019

(65) Prior Publication Data
US 2020/0216911 A1    Jul. 9, 2020

(51) Int. Cl.
*C12Q 1/6886* (2018.01)
(52) U.S. Cl.
CPC ..... *C12Q 1/6886* (2013.01); *C12Q 2600/154* (2013.01)
(58) Field of Classification Search
None
See application file for complete search history.

(56) References Cited

U.S. PATENT DOCUMENTS

| | | | | |
|---|---|---|---|---|
| 2012/0208180 A1* | 8/2012 | Durst | ............... | C12Q 1/6886 435/5 |
| 2015/0118681 A1* | 4/2015 | Kanai | ............... | C12Q 1/6886 435/6.11 |
| 2016/0300013 A1* | 10/2016 | Ashutosh | ............... | G16B 20/10 |

FOREIGN PATENT DOCUMENTS

| | | |
|---|---|---|
| JP | 2014-050390 A | 3/2014 |
| WO | WO 2011/032721 A1 | 3/2011 |
| WO | WO 2013/021279 A2 | 2/2013 |
| WO | WO 2013/039394 A1 | 3/2013 |
| WO | WO 2014/080017 A1 | 5/2014 |
| WO | WO 2016/048138 A1 | 3/2016 |
| WO | WO 2016/124177 A1 | 8/2016 |
| WO | WO 2017/019751 A1 | 2/2017 |
| WO | WO 2017/034407 A1 | 3/2017 |
| WO | WO 2019/063097 A1 | 4/2019 |

OTHER PUBLICATIONS

Feng (PNAS 2010 vol. 107 No 19 pp. 8689-8694) (Year: 2010).*
Cobb et al (Crit Care Med 2002 vol. 30 p. 2711) (Year: 2002).*
Verma et al. (Cancer Nov. 1, 2011 p. 4958) (Year: 2011).*
Fan et al. (Journal of Immunology Research 2014 pp. 1-14) (Year: 2014).*
De Strooper (Cancer Prev Res 2014 vol. 7 p. 1251) (Year: 2014).*
Sanchez-Vega et al., *Epigenetics*, 8(12): 1355-1372 (2013).
Yeh et al., *Oncotarget*, 6(30): 29555-29572 (2015).
European Patent Office, International Search Report in International Application No. PCT/EP2017/074829 (Jun. 1, 2018).
European Patent Office, Written Opinion of The International Searching Authority in International Application No. PCT/EP2017/074829 (Jun. 1, 2018).

* cited by examiner

*Primary Examiner* — Katherine D Salmon
(74) *Attorney, Agent, or Firm* — Neal, Gerber & Eisenberg LLP

(57) ABSTRACT

Methods for the determination of the risk of developing neoplasia in a tissue, preferably anogenital tissue, showing no histopathological indications of neoplasia are described. The method is based on the determination of the methylation status of genomic DNA sequences associated with the genes ZNF671, ZNF154, ZNF776, ASTN1, BRINP2, DLX1, METAP1D and/or DLX2.

33 Claims, 4 Drawing Sheets

Specification includes a Sequence Listing.

```
SEQUENCE LISTING

<160> NUMBER OF SEQ ID NOS: 9

<210> SEQ ID NO 1
<211> LENGTH: 23
<212> TYPE: DNA
<213> ORGANISM: Artificial Sequence
<220> FEATURE:
<223> OTHER INFORMATION: oligonucleotide

<400> SEQUENCE: 1
cggaggacgt agtatttatt cgc                                            23

<210> SEQ ID NO 2
<211> LENGTH: 20
<212> TYPE: DNA
<213> ORGANISM: Artificial Sequence
<220> FEATURE:
<223> OTHER INFORMATION: oligonucleotide

<400> SEQUENCE: 2
ctacgtcccc gatcgaaacg                                                20

<210> SEQ ID NO 3
<211> LENGTH: 27
<212> TYPE: DNA
<213> ORGANISM: Artificial Sequence
<220> FEATURE:
<223> OTHER INFORMATION: oligonucleotide

<400> SEQUENCE: 3
cgtgggcgcg gacagttgtc gggagcg                                        27

<210> SEQ ID NO 4
<211> LENGTH: 21
<212> TYPE: DNA
<213> ORGANISM: Artificial Sequence
<220> FEATURE:
<223> OTHER INFORMATION: oligonucleotide

<400> SEQUENCE: 4
cgtaagcgtt gttagcgtag c                                              21

<210> SEQ ID NO 5
<211> LENGTH: 21
<212> TYPE: DNA
<213> ORGANISM: Artificial Sequence
<220> FEATURE:
```

<223> OTHER INFORMATION: oligonucleotide

<400> SEQUENCE: 5
cgcgaaatcg aaacgaaaac g    21

<210> SEQ ID NO 6
<211> LENGTH: 28
<212> TYPE: DNA
<213> ORGANISM: Artificial Sequence
<220> FEATURE:
<223> OTHER INFORMATION: oligonucleotide

<400> SEQUENCE: 6
gtaattcgtt tgtttcgtaa gttgttcg    28

<210> SEQ ID NO 7
<211> LENGTH: 21
<212> TYPE: DNA
<213> ORGANISM: Artificial Sequence
<220> FEATURE:
<223> OTHER INFORMATION: oligonucleotide

<400> SEQUENCE: 7
tatcgggatt cgcgtttgta c    21

<210> SEQ ID NO 8
<211> LENGTH: 23
<212> TYPE: DNA
<213> ORGANISM: Artificial Sequence
<220> FEATURE:
<223> OTHER INFORMATION: oligonucleotide

<400> SEQUENCE: 8
cgaccgaact aaaactcaac tcg    23

<210> SEQ ID NO 9
<211> LENGTH: 27
<212> TYPE: DNA
<213> ORGANISM: Artificial Sequence
<220> FEATURE:
<223> OTHER INFORMATION: oligonucleotide

<400> SEQUENCE: 9
cgtaaacgtt agctgttctg gaaaccg    27

RISK DETERMINATION FOR NEOPLASIA AND CANCER

CROSS-REFERENCE TO RELATED APPLICATIONS

This application is a National Stage Entry of International Application Number PCT/EP2017/074829, which was filed on Sep. 29, 2017, the entire contents of which are incorporated herein by reference.

TECHNICAL FIELD OF THE INVENTION

The present invention relates to a method for determining the risk of developing neoplasia in the tissue of a patient which tissue does not show any histopathological indication of neoplasia, i.e., does not show any morphological changes (dysplasia). In particular, the method involves determining the methylation status of one or more regions of genomic DNA associated with the genes ZNF671, ZNF154, ZNF776, ASTN1, BRINP2, DLX1, METAP1D and/or DLX2 in a biological sample obtained from the patient, wherein when the one or more regions associated with the genes ZNF671, ZNF154, ZNF776, ASTN1, BRINP2, DLX1, METAP1D and/or DLX2 is methylated in the sample, the patient has an increased risk for developing neoplasia in the tissue.

BACKGROUND OF THE INVENTION

Cancer of the cervix uteri (cervical carcinoma) is the second most frequent malignant cancerous disease in women world-wide. It often develops in the course of an infection with so-called high-risk human papilloma viruses (hr-HPV) via preliminary stages, which stages are referred to as cervical intraepithelial neoplasias (CIN). These stages are divided into three levels according to severity of involvement:

CIN1=mild dysplasia, goes from basal to a maximum of one third of the height of the epithelium;
CIN2=moderate dysplasia, up to two-thirds of the height of the epithelium; and
CIN3=high-grade dysplasia, penetrates almost the entire layer of the epithelium.

In connection with these various dysplasias, there is a significant risk that they will develop into cervical carcinoma. However, while approximately 90% of the CIN1 dysplasias resolve within a certain time and the underlying hr-HPV infection is no longer detectable, approximately 30% of the CIN2 dysplasias and between 30 and 50% of the CIN3 dysplasias develop into cervical carcinoma if left untreated. In other words, not every CIN1, CIN2 or CIN3 dysplasia develops into a malignancy, i.e., cervical carcinoma, but many do (see e.g., Cuzick et al., 2006, Int J Cancer 119:1095-1101).

The existing test for the detection of a cervical carcinoma and its preliminary stages (CINs) is based on a cytomorphological method (the Pap test). However, the Pap test is highly error-prone since a few cells suspected of being cancerous or involved in dysplasia must be recognized against a background of thousands of other, different cells by means of microscopy. In addition, the evaluation of cell morphology is extremely subjective. As a result of these weaknesses, the sensitivity of the Pap test is 53% for the detection of precancerous stage CIN2, CIN3, and cancer, and the specificity is 96.3% (Cuzick et al., 2006, Int J Cancer 119:1095-1101).

Molecular biology testing has significantly improved cancer care in many areas. Since, with a few exceptions, all cervical carcinomas and their precursors contain hr-HPV DNA, the detection of HPV DNA appears as the ideal method for detection of cancer. Various published studies have shown that HPV DNA detection for detection of CIN2 has a sensitivity greater than 95% and a specificity greater than 90%. However, a positive HPV test causes many women to worry unnecessarily since only a small proportion of the infected women will go on to develop cancer, and since most of whom infected with HPV do not have cancer precursors/dysplasia (Cuzick et al., 2006, Int J Cancer 119:1095-1101).

Many publications have shown that methylation markers are generally suitable for molecular diagnostics in the field of early detection of the cervical carcinoma. For example, Wang et al., 2008, Cancer Res. 68:2489 describe the identification of new methylation markers in cervical carcinoma. Further, Huang et al., 2008, Abstract #50, 99th Annual Meeting of the American Association for Cancer Research, San Diego, CA, USA describe the hypermethylation of CIDEA and RXFP3 as potential epigenetic markers for ovarian cancer.

EP Patent No. 2 478 117 B1 describes detection of hypermethylation of the promoter/5'-regions of the ASTN1 and ZNF671 genes for the detection of CIN3 and cervical carcinomas and Hansel et al., 2014, PLoS ONE 9(3):e91905 describe the use of DNA methylation markers for the triage of high-risk papillomavirus DNA-positive women, which methylation markers are DLX1, ITGA4, RXFP3, SOX17, and ZNF671.

There are many diagnostic methods which are useful for determining the likelihood that an observed neoplasia will develop into a carcinoma or whether an observed neoplasia actually is malignant carcinoma. Nonetheless, there remains a need in the art for methods to determine the risk for developing neoplasia and/or carcinoma in patients where there is yet no histopathological indication of neoplasia in the tissue. The present invention described below fulfills this need.

SUMMARY OF THE INVENTION

The present invention is based, at least in part, on the inventors' discovery that the methylation status of genomic DNA sequences associated with one or more of the genes ZNF671, ZNF154, ZNF776, ASTN1, BRINP2, DLX1, METAP1D and/or DLX2 in a biological sample obtained from a patient is predictive of whether a tissue of the patient will develop neoplasia, in particular, a high-grade neoplasia which has a significant potential to develop into a carcinoma, in cases where the tissue shows no histopathological or cytomorphological indication of neoplasia, e.g., at the time the sample was obtained.

The present invention is directed to a method for determining the risk for developing neoplasia in a tissue of a patient which tissue shows no histopathological indication of neoplasia, comprising determining the methylation status of one or more regions of genomic DNA associated with the genes ZNF671, ZNF154, ZNF776, ASTN1, BRINP2, DLX1, METAP1D and/or DLX2 in a biological sample obtained from the patient. In an embodiment, when the one or more regions is methylated in the biological sample, the patient has an increased risk for developing neoplasia in the tissue. In one embodiment, the methylation status of a region of genomic DNA associated with the gene ZNF671 can be preferably determined. In certain embodiments, the increased risk can be one in that a moderate or severe form of neoplasia, i.e., HSIL/CIN3, having a significant potential to develop into a carcinoma, will develop in the tissue within 3 to 6 months, or within 7 to 12 months, or within 13 to 24 months, or within 24 to 36 months after the biological sample that was used to determine the methylation status was obtained.

In the context of the present invention, determining the methylation status encompasses determining the methylation status of genomic DNA sequences associated with the ZNF671, ZNF154, ZNF776, ASTN1, BRINP2, DLX1, METAP1D and/or DLX2 genes, or a portion of such sequences, including both coding and non-coding sequences within the gene(s). Also encompassed are sequences located 5' to the transcriptional start site of the gene(s), i.e., promoter/enhancer sequences that control the expression of the genes, as well as non-coding sequences located 3' of the encoding DNA region. In an embodiment, the methylation status of one or more coding exon sequences of the genomic DNA of ZNF671, ZNF154, ZNF776, ASTN1, BRINP2, DLX1, METAP1D and/or DLX2 or a portion thereof can be determined. In an embodiment, the methylation status of one or more non-coding intron sequences of the genomic DNA of ZNF671, ZNF154, ZNF776, ASTN1, BRINP2, DLX1, METAP1D and/or DLX2 or a portion thereof can be determined. In an embodiment, the methylation status of the promoter region of ZNF671, ZNF154, ZNF776, ASTN1, BRINP2, DLX1, METAP1D and/or DLX2 or a portion of the promoter region can be determined. In a preferred embodiment, the one or more regions of genomic DNA associated with the specified genes whose methylation status is to be determined comprises a CpG island. In an embodiment, the genomic DNA associated with the specified genes whose methylation status is to be determined comprises those genomic DNA sequences within approximately 1, 2, 3, 4, 5, 6, 7, 8, 9, 10, 15, 20, 25, 30, 35 or 40 kilobases upstream and/or downstream (5' and/or 3') of the sequence of the specified gene.

In an embodiment, the methylation status can be compared to the methylation status of a control sample. A control sample can be a sample obtained from a tissue in which it is known that at least one, two, three or all of the (respective) genomic sequences associated with ZNF671, ZNF154, ZNF776, ASTN1, BRINP2, DLX1, METAP1D and/or DLX2 is not methylated or can be a standard reflecting a known value or status of methylation. A control sample can also be a biological sample obtained from a different patient, in which it has been determined that the tissue in that patient did not develop neoplasia, e.g., did not develop neoplasia within three years or later after the sample from the different patient was obtained.

In one embodiment, the neoplasia can be intraepithelial neoplasia. Preferably, the neoplasia can be anogenital neoplasia, more preferably cervical or uterine neoplasia. In one embodiment, the cervical neoplasia can be a HSIL/CIN3 cervical neoplasia or cervical cancer. In a preferred embodiment, the method of the invention is directed to determining the risk for developing a high-grade intraepithelial lesion or CIN3 neoplasia in, e.g., anogenital tissue, such as cervical or rectal tissue.

In an embodiment, the biological sample obtained from the patient can contain cells of the tissue. In an embodiment, the biological sample can be a cervical or rectal smear, e.g., a Pap smear, comprising cells of the cervix or rectum. In an embodiment, the biological sample can be blood, sputum, bronchial aspirate, urine, stool, bile, gastrointestinal secretions, or lymph fluid.

In an embodiment, the tissue can be cervical, vaginal, urethral, anogenital, rectal, throat, mouth, nasal, stomach, skin, liver, pancreatic or muscle tissue. In an embodiment, the biological sample can be obtained directly from the tissue for which the risk of developing neoplasia is to be determined.

In an embodiment, the histopathological state of the tissue can be determined colposcopically.

In one embodiment of the invention, the biological sample obtained from the patient can be used to determine the methylation status of one or more regions of genomic DNA associated with the genes ZNF671, ZNF154, ZNF776, ASTN1, BRINP2, DLX1, METAP1D and/or DLX2 and to determine the histopathological state of the tissue. In another embodiment, the biological sample obtained from the patient used to determine the methylation status of one or more regions of genomic DNA associated with the genes ZNF671, ZNF154, ZNF776, ASTN1, BRINP2, DLX1, METAP1D and/or DLX2 can be a different biological sample obtained from the patient than the biological sample used to determine the histopathological state of the tissue. The different biological samples can be obtained in the same or similar manner and/or can be of the same or similar nature, e.g., the two samples can both be smears of cervical tissue. Also, the different biological samples can be obtained in a different manner and/or can be of a different nature, e.g., one sample can be a smear of cervical tissue and the other a biopsy of cervical tissue.

In an embodiment, the biological sample obtained from the patient used to determine the methylation status can be obtained after the histopathological state of the tissue has been determined. In an embodiment, the biological sample obtained from the patient used to determine the methylation status can be obtained before the histopathological state of the tissue has been determined.

In an embodiment, the patient can be infected with a papillomavirus or can be free of infection from a papillomavirus.

In an embodiment, the methylation status can be determined by methylation-specific PCR (MSP), preferably wherein the MSP is a quantitative MSP (QMSP), preferably wherein the QMSP is based on the use of fluorescent probes. In an embodiment, the methylation status can be determined by nanopore sequencing.

In an embodiment of the present invention, where after the tissue has been determined to have an increased risk for developing neoplasia, the method further comprises determining the histopathological state of the tissue. The further determining can take place, e.g., within 3 months, 6 months, 9 months, or 12 months after the determination of an increased risk for developing neoplasia. For example, the further determining of the histopathological state of the tissue can occur by histopathologically screening a sample of the tissue obtained from the patient after the determination of an increased risk. The sample of tissue can be obtained, e.g., within 3 months, 6 months, 9 months, or 12 months after the determination of an increased risk of neoplasia.

In another embodiment, where after the tissue has been determined to have an increased risk for developing neoplasia, the method can further comprise administering to the patient a medicament to prevent development of a neoplasia or cancer in the tissue. Any such medicament known in the art suitable for preventing neoplasia can be administered to the patient having an increased risk for developing neoplasia. In an embodiment, the medicament is an anti-inflammatory agent, preferably a non-steroidal anti-inflammatory agent or the medicament is a methylation inhibitor, such as azacytidine or decitabine. In an embodiment, where the tissue is anogenital tissue, e.g., cervical or rectal tissue, the patient having the increased risk for developing neoplasia can be treated by vaccinating the patient against papillomavirus, e.g., human papillomavirus. In an embodiment, the papillomavirus to be vaccinated against preferably can be a strain of the virus known to cause or contribute to causing cancer, such as HPV strains 16 and 18.

The present invention also is directed to a method for selecting a patient showing no histopathological indication of neoplasia in a tissue to undergo more frequent screening for neoplasia in the tissue, comprising selecting a patient in which one or more regions of genomic DNA associated with the genes ZNF671, ZNF154, ZNF776, ASTN1, BRINP2, DLX1, METAP1D and/or DLX2 is methylated in a biological sample obtained from the patient. In an embodiment, the more frequent screening can be histopathology-based screening of the same tissue. Preferably, the more frequent screening can take place between every 3 to 12 months, preferably every 6 months, more preferably every 3 months.

The present invention is directed to a method for determining the risk for developing neoplasia in a tissue showing no histopathological indication of neoplasia, comprising (i) determining the histopathological state of a tissue of a patient; and (ii) determining the methylation status of one or more regions of genomic DNA associated with the genes ZNF671, ZNF154, ZNF776, ASTN1, BRINP2, DLX1, METAP1D and/or DLX2 in a biological sample obtained from the same patient before or after step (i). In an embodiment, when the histopathological state of the tissue indicates an absence of neoplasia, and when the one or more regions associated with the genes ZNF671, ZNF154, ZNF776, ASTN1, BRINP2, DLX1, METAP1D and/or DLX2 is methylated in the biological sample, the patient has an increased risk for developing neoplasia in the tissue.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention, which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H.G.W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., Molecular Cloning: A Laboratory Manual, 4th Edition, M. R. Green, J. Sambrook et al. eds., Cold Spring Harbor Laboratory Press, Cold Spring Harbor 2012).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e., the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention, inter alia, allows for the identification of patients who have an increased risk for developing neoplasia, in particular a high-grade neoplasia, in a tissue, which tissue does not show any histopathological indications of neoplasia. The identification of such patients is due to the fact that in tissues showing no indications of neoplasia but where genomic DNA sequences associated with one or more of the ZNF671, ZNF154, ZNF776, ASTN1, BRINP2, DLX1, METAP1D and/or DLX2 genes are methylated in a biological sample obtained from the patient, a significantly increased risk for developing neoplasia in the tissue, e.g., HSIL/CIN3, exists. Once such patients having the increased risk for developing neoplasia in the tissue have been identified, such patients can be monitored more frequently for the appearance of neoplasia in the tissue using standard histopathological methods in order to increase the likelihood of early detection and/or can be treated to prevent the development of neoplasia in the tissue.

The genes associated with the genomic DNA sequences for which the methylation status is determined in accordance with the present invention include the following:

ASTN1 (Astrotactin 1; GenBank accession numbers NM_0043.1, NM_207108, contained in NC_000001.9), which is an adhesion protein which plays an important part in the migration of neuronal cells;

BRINP2 (Bone morphogenetic protein/retinoic acid inducible neural-specific protein; GenBank accession number NM_021165.3, contained in NC_000001.11);

ZNF671 (GenBank accession number NM_024883, contained in NC_000019.9), which is a transcription factor having a typical zinc finger motif;

ZNF154 (GenBank accession number NP_001078853.1, contained in NC_000019.10), which is a protein having a typical zinc finger motif;

ZNF776 (GenBank accession number NP_775903.3, contained in NC_000019.10), which is a protein having a typical zinc finger motif;

DLX1 (distal-less homeobox 1; GenBank accession numbers NM_178120, NM_001038493, contained in NC_000002.11), which is a transcription factor and may influence the cell differentiation;

DLX2 (distal-less homeobox gene 2a; GenBank accession number NP_004396.1, contained in NC_000002.12), which is postulated to play a role in development; and METAP1D (GenBank accession numbers NM_001322279.1, NM_199227.2, NM_001322278.1, NR_136276.1, NR_136273.1, contained in NC_000002.12), a methionyl aminopeptidase type 1D.

In certain embodiments of the invention where the subject is a non-human subject, the genes associated with the sequences for which the methylation status is determined will be the respective homologous genes in the respective non-human subject. In an embodiment relating to non-human subjects, the genomic DNAs are those regions in the non-human chromosome(s) having the strongest homology/identity with the human sequences of the respective genes and/or any portion thereof.

In an embodiment, the one or more regions of genomic DNA associated with the specified genes whose methylation status is to be determined comprises those genomic DNA sequences within approximately 0.5, 1, 2, 3, 4, 5, 6, 7, 8, 9, 10, 15, 20, 25, 30, 35 or 40 kilobases upstream and/or downstream (5' and/or 3') of the sequence of at least one of the specified genes. In an embodiment of the present invention, the one or more regions of genomic DNA sequences associated with the genes ZNF671, ZNF154, ZNF776, ASTN1, BRINP2, DLX1, METAP1D and/or DLX2 include a portion of human chromosome 1 from approximately nucleotide 177,132,585 to approximately nucleotide 177,152,584, a portion of human chromosome 2 from approximately nucleotide 172,943,500 to approximately nucleotide 172,974,289, and/or a portion of human chromosome 19 from approximately nucleotide 58,217,499 to approximately nucleotide 58,262,501, as well as portions or fragments of such sequences (see FIGS. 1, 2A, 2B and 3). The nucleotide numbers (positions) recited herein are from the Human Genome Assembly of February 2009 (GRCh37/hg19).

Preferably, a portion of the foregoing sequences comprises a CG-rich region and/or a CpG island contained within the larger sequence. Thus, in an embodiment, the one or more regions of genomic DNA associated with the specified genes are one or more portions of the above-specified chromosomal sequences, in which the one or more portions comprise a CG-rich region and/or a CpG island. In certain embodiments, the portion of the genomic sequences associated with ASTN1 and/or BRINP2 includes the region from about nucleotide 177,140,121 to about nucleotide 177,140,323 of human chromosome 1, the portion of the genomic sequences associated with METAP1D, DLX1, and/or DLX2 includes the region from about nucleotide 172,945,912 to about nucleotide 172,946,212 of human chromosome 2, and the portion of the genomic sequences associated with ZNF154, ZNF671, and/or ZNF776 includes the region from about nucleotide 58,238,586 to about nucleotide 58,239,028 of human chromosome 19, as well as portions or fragments of such regions.

In determining the methylation status of these regions of genomic DNA sequences or portions thereof, the methylation state of single, e.g., isolated, cytosines contained within these sequences can be determined, as well as the methylation state of cytosines in CG-rich regions and in CpG islands contained within these sequences. In a preferred embodiment, the methylation status of the one or more regions of genomic DNA associated with the specified genes is determined by measuring the methylation state of cytosines in one or more CpG islands contained within such genomic sequences. In one embodiment, a region of a genomic DNA sequence associated with one or more of the specified genes whose methylation status is to be determined comprises at least one of the CpG islands indicated in any of FIGS. 1 to 3 or a portion thereof.

As used herein, the terms "portion", "fragment" and "part" are used interchangeably and refer to a fraction, in particular to a fraction of a larger nucleotide or amino acid sequence. Also encompassed within these terms is a molecule that comprises multiple discontinuous portions of a larger molecule, e.g., a nucleotide sequence which comprises one or more discontinuous portions of a different nucleotide sequence, such as a chromosomal sequence. In certain embodiments, a portion of a nucleotide sequence can be about 10, 20, 30, 40, 50, 100, 150, 200, 300, 400, 500, 600, 700, 800, 900, 1000, 1500, 2000, 2500, 3000, 3500, 4000, 4500, 5000, 6000, 7000, 8000, 9000, or about 10,000 nucleotides or more in length. In another embodiment, a portion of the chromosomal sequences of chromosomes 1, 2 or 19 comprises at least one CpG island or a portion of the CpG island. Exemplary CpG islands encompassed by the invention are identified in FIGS. 1 to 3, and optionally include sequences of up to 1000 nucleotides upstream and/or downstream of the CpG islands.

The tissue for which the risk for developing neoplasia is to be determined according to the present invention can be any tissue of the patient. Exemplary tissues include, but are not limited to cervical, vaginal, urethral, anogenital, rectal, penial, throat, mouth, nasal, stomach, intestinal, skin, liver, pancreatic, lung, nerve/neuronal and muscle tissue. In a preferred embodiment, the tissue is anogenital tissue, e.g., cervical, vaginal, or rectal tissue.

Although the terms "neoplasia" and "dysplasia" have different meanings, these terms are used interchangeably/synonymously herein since they both refer to morphological or histological changes in a tissue and/or in cells of a tissue. Neoplasia refers to the development of tumors or cancerous tissue. Dysplasia refers to changes in the morphological characteristics and/or functions of cells and tissues, such as an increase in the number of immature cells and greater variability between the cells. Dysplasia does not necessarily show that the cells have become cancerous, but rather does indicate that the underlying changes may predispose to cancer.

Dysplasia can be divided into different levels according to severity of involvement, e.g., (i) mild dysplasia, changes extend from the basal layer to a maximum of one third of the height of the epithelium layer of the tissue; (ii) moderate dysplasia, changes extend up to two-thirds of the height of the epithelium; and (iii) high-grade dysplasia, in which changes are seen within almost the entire layer of the epithelium of the tissue. Mild dysplasia also may be referred to as low-grade intraepithelial lesion (LSIL) and moderate or severe dysplasia also may be referred to as high-grade intraepithelial lesion (HSIL).

In connection with cervical tissue, dysplasia can be referred to as a cervical intraepithelial neoplasia (CIN), which can be divided into different levels according to severity of involvement: CIN1=mild dysplasia; CIN2=moderate dysplasia; and CIN3=high-grade dysplasia. CIN1 also can be referred to as low-grade intraepithelial lesion (LSIL) and CIN2/CIN3 also can be referred to as high-grade intraepithelial lesion (HSIL).

In the context of the present invention, LSIL is used interchangeably with CIN1, and HSIL is used interchangeably with CIN2 and/or CIN3.

Whether or not a tissue shows any indication of neoplasia can be determined using any appropriate method known in the art for determining the histopathological or cytomorphological state of a tissue or cells within a tissue, such as under a microscope or colposcopically. For example, a sample of the tissue obtained from the patient can be processed for viewing under a microscope by fixing and staining the sample of tissue, using, e.g., formalin and a combination of hematoxylin and eosin. Hematoxylin is used to stain nuclei blue, while eosin stains cytoplasm and the extracellular connective tissue matrix pink. Other compounds used to color tissue sections include safranin, Oil Red O, Congo red, silver salts and artificial dyes. Antibodies can also be used to stain particular proteins, lipids and carbohydrates of cells, e.g. antibodies against p16 or Ki67. These same methods can be used in the analysis of the tissue from patients determined to have an increased risk for developing neoplasia.

The terms "subject", "individual", "organism" or "patient" are used interchangeably and relate to vertebrates, preferably mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" also includes humans. Preferably, the terms "subject", "individual", "organism" or "patient" refer to male and female mammals, in particular male and female humans. The subject can be of any age, however, it is preferred that the subject be an adult. In an embodiment, the subject is 30 years old or younger. In another embodiment, the subject is older than 30 years. In an embodiment, the subject is a human female, preferably a human female preferably between 12 and 30 years old. In an embodiment, the subject is or has been sexually active. In certain embodiments, the subject can be infected with a papillomavirus or can be free of infection of a papillomavirus.

The term "in vivo" relates to the situation in a subject.

As used herein, "biological sample" includes any biological sample obtained from a patient. Examples of such biological samples include blood, smears of cells, sputum, bronchial aspirate, urine, stool, bile, gastrointestinal secretions, lymph fluid, bone marrow, organ aspirates and tissue biopsies, including punch biopsies. Optionally, the biological sample can be obtained from a mucous membrane of the patient. Smears containing cells are preferred. The biological sample preferably can contain cells from the tissue for which the increased risk of developing neoplasia is to be determined. Preferably, the biological sample contains DNA, e.g., genomic DNA, such that the methylation status of the DNA or a portion thereof can be determined. The biological sample can be one that is obtained from the tissue for which the risk of developing neoplasia is to be determined.

Tissues of the patient from which the biological sample can be obtained include, but are not limited to, cervical, vaginal, urethral, anogenital, rectal, penial, throat, mouth, nasal, stomach, intestinal, skin, liver, pancreatic, lung and muscle. In one embodiment, the biological sample is obtained directly from a particular tissue/organ, for example, from the cervix (cervix uteri) of the patient. In one embodiment, the biological sample is obtained from the rectum of the patient. Any suitable method for obtaining biological sample from the patient and/or from an appropriate tissue can be used in connection with the present invention.

By "being at risk" or "has an increased risk" is meant a subject, i.e., a patient, that is identified as having a higher than normal chance of developing a disease, in particular neoplasia or cancer, compared to the general population. In an embodiment, the increased risk means developing neoplasia within 1 to 3 months of the sample being obtained. In an embodiment, the increased risk means developing neoplasia within 3 to 6 months of the sample being obtained. In an embodiment, the increased risk means developing neoplasia within 7 to 12 months of the sample being obtained. In an embodiment, the increased risk means developing neoplasia within 13 to 24 months of the sample being obtained. In an embodiment, the increased risk means developing neoplasia within 24 to 36 months of the sample being obtained. In an embodiment, the increased risk means developing neoplasia 36 months, e.g., 42, 48, 52, 60 months or later, after the sample has been obtained.

In accordance with the present invention, the genomic DNA present in the sample can be processed in some manner in order to determine the methylation status of genomic DNA sequences associated with one or more of the genes ZNF671, ZNF154, ZNF776, ASTN1, BRINP2, DLX1, METAP1D and/or DLX2. For example, the genomic DNA can be extracted from the biological sample and the methylation status of a particular region of the DNA can be determined using any method known to the skilled artisan, e.g., extraction with phenol/chloroform or by means of commercial kits and then determining the methylation using the sodium bisulfite method or by means of a commercial kit, such as the EZ-DNA Methylation-Gold™ kit, Zymo Research, Irvine, California. In another embodiment, the methylation status can be determined without the need for a preparatory step of DNA isolation from the sample.

The term "methylation status" in general refers to whether or not genomic DNA or a region thereof contains methylated nucleotide residues, in particular methylated cytosine residues, i.e., 5-methylcytosine. In an embodiment, a region of genomic DNA whose methylation status is to be determined is one that is rich in guanine and cytosine residues, and in particular is rich in CG-dinucleotides, i.e., the region contains one or more CpG islands. The methylation status can be determined by means of known methods, as discussed below. Methylation often occurs in promoter regions of genes, and thus, methods for the detection of the methylation status of relevant genes are usually concentrated in these regions. However, genes also can be methylated in regions other than the promoter region, since GC-rich areas such as those containing CpG islands can be located in other regions of the genes. The detection of the methylation status of such other regions of the genes is also encompassed within the present invention.

In the method according to the invention, the methylation status of preferably CG-rich regions, e.g., CpG islands, in the genomic DNA associated with the genes ZNF671, ZNF154, ZNF776, ASTN1, BRINP2, DLX1, METAP1D and/or DLX2 is determined. The term "methylation" is considered to be synonymous with the term "hypermethylation" as commonly known in molecular biology. It refers to the positive methylation status of the DNA, i.e., the presence of 5-methylcytosine in the DNA, preferably within a CpG island or other region rich in GC nucleotides.

As discussed above, the region of genomic DNA whose methylation status is to be determined can be located in an exon, in an intron, or in the 5' promoter/enhancer region of one of the specified genes. As used herein, the term "is methylated" at least means that the DNA sequence contains 5-methylcytosine nucleotides. In one embodiment, the increased risk for developing neoplasia is determined by the presence of 5-methylcytosine nucleotides in the DNA sequence tested (for which the methylation status was determined). In an embodiment, the increased risk for developing neoplasia is determined by an increase in the amount of 5-methylcytosines (methylation) in the DNA sequence tested. The increase in the amount of methylation can be determined by comparing the amount of methylation in the biological sample to the amount of methylation determined in a control sample. In an embodiment, the increased risk for developing neoplasia is determined where the increase in methylation is at least 5%, 10%, 15%, 20%, 25%, 50%, 75%, 100%, 150%, 200% or more over the amount of methylation determined in the control sample. In an embodiment, the increased risk for developing neoplasia is determined where the increase in methylation is at least 1.5×, 2×, 3×, 4×, 5×, 6×, 7×, 8×, 9×, 10×, 20×, 30×, 40×, 50× or more over the amount of methylation determined in the control sample. In one embodiment, an increase in level of methylation is determined by whether or not the level of methylation in the biological sample exceeds a predetermined threshold level. A control sample can be a gene/sequence which is known to be either methylated or non-methylated, or can be the same sequence tested in the biological sample obtained from the patient but which same sequence was obtained from another patient, wherein which tissue in the other patient was determined not to develop neoplasia within a specified time period after the sample from the other patient was obtained. In certain embodiments, the specified time period can be at least 24 months, 30 months, 36 months, or 48 months or longer.

In an embodiment, the methylation status of the DNA is determined using nanopore sequencing, which interprets changes in ionic currents observed when single DNA molecules pass through a nanometer-size protein pore. In addition, nanopore sequencing is able to discriminate not only the nucleotides of a strand of DNA but also single base modifications, such as 5'-methylated cytosine. In view of these abilities, concurrent analysis of sequence identity and methylation of cytosines can be carried out, see, e.g., Euskirchen et al., 2017, Acta Neuropathol, epub prior to publication, DOI 10.1007/S00401-017-1743-5.

The methylation status of the DNA also can be determined after a preceding modification of non-methylated cytosine residues by the bisulfite method by means of what is called a methylation-specific PCR reaction (MSP) using suitable primer pairs. In the bisulfite method, non-methylated cytosine residues are converted into uracil using sodium bisulfite, whereas methylated cytosine residues (5-methylcytosine) are protected against this conversion. Since uracil has pairing properties differing from that of cytosine, i.e., it behaves like thymine pairing with adenosine, the conversion can be detected using specifically designed primers based on the fact that uracil binds thymine and cytosine does not bind thymine. MSP is an established technique known in the art for the detection of DNA methylation.

In the context of the present invention, the design of the PCR amplification primers used for the detection of the methylation status will depend on the location of the sequence within the genomic DNA sequence associated with one or more of the genes ZNF671, ZNF154, ZNF776, ASTN1, BRINP2, DLX1, METAP1D and/or DLX2 whose methylation status is to be determined. For example, methylation-specific primers for such sequences can be designed to bind only to the bisulfite-modified sample DNA if certain cytosines were methylated within the primer binding sites. If these regions were not methylated before the bisulfite treatment, then the primers will not bind and no PCR reaction product is formed. Thus, in the context of the present invention, the presence of a PCR reaction indicates that the particular DNA region of the particular gene is methylated, and thus, that the patient has an increased risk for developing neoplasia in the tissue.

A real-time PCR method (QMSP), which does not only permit a qualitative detection of the methylation but also a quantification of the methylated DNA regions, is particularly preferred. This MSP can be carried out in a fluorescence-based real-time method where the formation of the methylation-specific product is detected by the incorporation of a fluorescent dye, e.g., SYBR®-Green I or II (ThermoFisher Scientific, Waltham, MA) or EVA-Green® (Biotium, Inc., Fremont, CA). These methods are able to detect regions of methylated DNA in a large background of non-methylated DNA and are high-throughput methods particularly suitable for screening tissue samples (Shames et al., 2007, Cancer Lett, 251:187-198).

Alternatively, the production of PCR products by MSP can also be detected by a hybridization method after completion of the PCR, e.g., using strips or arrays with fixed probes to which the resulting PCR products bind and thus can be detected. Other techniques, include the use of methylation-sensitive DNA restriction enzymes to differentiate between methylated and non-methylated DNA or the high-throughput sequencing of DNA chemically treated with bisulfite for the detection of methylated DNA.

Another preferred method is a QMSP method based on the "MethyLight" technique, in which fluorescent probes are used for the respective regions of DNA to be tested for methylation. In a preferred example, a probe carries a fluorescent dye marker at the 5'-end and a quencher at the 3'-end, which probe binds to the PCR reaction product between the two specific amplification primers (see, e.g., Eads et al., 2000, Nucleic Acids Research 28:e32). Fluorescent dye is released as soon as the probe is decomposed after binding to the target sequence by the 5'-3'-exonuclease activity of DNA polymerase and the measured fluorescence reflects the amount of product formed. The number of reactions to be carried out can be correspondingly reduced for samples to be investigated in this method by using several oligonucleotides and probes (Shames et al., 2007, Cancer Lett 251:187-198). Suitable fluorescent dyes and quenchers are known in the art, e.g., fluorophore FAM™, HEX™, NED™, ROX™, Texas Red®, etc., and quenchers TAMRA™ or Black Hole Quencher®, available, for example, at ATDBio Ltd., Southhampton, UK or LGC Biosearch Technologies, Steinach, Germany.

In a particularly preferred embodiment, the determination of the methylation status can be carried out as a multiplex experiment. Such a multiplex experiment permits the analysis of the methylation status of several regions of genomic DNA in a sample, which are known to be correlated with an increased risk for developing neoplasia in a single assay. The multiplex method offers several advantages since the methylation status of the DNA region(s) set to be tested can be determined in one or two reactions per sample. This saves considerable time, sample material and material costs. In certain multiplex experiments, the methylation status of up to five genes can be determined. In addition, one further specific oligonucleotide each, the "probe", is used for each gene. The probe carries at one end a fluorescent dye and is designed such that the fluorescent signal is not detected until the probe specifically binds to the PCR reaction products formed. The different probes will carry different fluorescent groups and therefore each fluorescent signal can be detected simultaneously. Such methods also can be carried out by means of "microarray" technology.

Other methods known in the art for determining the methylation status can be used in accordance with the invention, e.g., methods based on a direct determination of the amount of specific product by fluorescence. For example, molecular beacon technology can also be used herein. Molecular beacons are oligonucleotides which are linked to both a reporter fluorophore and a quencher. The nucleotides at the 5'-end of the probe are complementary to those at the 3'-end so as to form a secondary structure characteristic of molecular beacons. In this state, which is referred to as a hair-pin or loop structure, no fluorescence is detected due to the proximity of the fluorophore to the quencher. The distance between fluorophore and quencher is increased as a result of the binding of the loop structure to a complementary DNA sequence, which is generated during PCR, and thus fluorescence can be observed.

Another suitable technique includes the "scorpion" technology. Scorpion probes are complex oligonucleotides which combine the properties of real-time PCR probes and PCR primers in one (single-scorpion) or two molecules (bi-scorpion). Similar to the molecular beacons, they include a characteristic secondary structure having a self-complementary region whose ends were modified with a reporter fluorophore and a quencher. In addition, these probes can be used as PCR primers. During a PCR cycle, reporter fluorescence can be observed by the attachment of the loop structure to a complementary DNA sequence since binding increases the distance between the quencher and reporter fluorophore. For the detection of binding of different probes, the different probes can have different reporter fluorophores.

Furthermore, positive and/or negative control DNA, e.g., a non-methylated control region of DNA, can be co-amplified and used for controlling the PCR reaction and/or controlling for the presence and/or absence of methylation.

Moreover, it is known that the methylation of regions of genomic DNA is often connected with a transcription blockade of genes in proximity with these regions of (methylated) DNA such that the encoded protein of the methylated gene is not expressed. Thus, in an embodiment, an indirect determination of the methylation status of one or more of the specified regions of genomic DNA can be accomplished by determining the concentration of the encoded RNA and/or protein of one or more of the ZNF671, ZNF154, ZNF776, ASTN1, BRINP2, DLX1, METAP1D and/or DLX2 genes. The detection thereof can be done by any appropriate method known in the art, e.g., (for RNA) Northern blot analysis, RT-PCR, etc., and (for proteins) antibody-based methods or methods which are based on the determination of a biological activity of the expressed protein.

As an illustrative example, the method according to the present invention comprises the following steps: (a) isolating DNA according to a standard method from a biological sample obtained from a patient, e.g., a smear containing cells of the tissue for which the risk for developing neoplasia is to be determined, e.g., using QiaAmp DNA-Mini kit (QIAGEN, Hilden, Germany); (b) chemically converting the isolated DNA according to the bisulfite method, e.g., by means of a commercial kit such as the EZ-DNA Methylation-Gold™ kit, Zymo Research, Irvine, California), which converts non-methylated cytosines in the DNA sample to uracils by treatment with sodium bisulfite and subsequent alkaline hydrolysis; (c) amplifying the relevant DNA by means of specific PCR primers for the methylated form of the DNA; and (d) detecting the presence of PCR products, which indicates that the DNA was methylated in the obtained sample.

Where the methylation of a region of the genomic DNA associated with one or more of the genes ZNF671, ZNF154, ZNF776, ASTN1, BRINP2, DLX1, METAP1D and/or DLX2 is to be determined using a methylation-specific PCR or QMSP protocol, the following exemplary methylation-specific amplification primers can be used, optionally with the exemplary probe oligos for detecting the potential amplification product:

| Gene | Forward primer | Reverse primer | Fluorescent Probe oligo |
| --- | --- | --- | --- |
| ZNF671 | CGGAGGACGTAG TATTTATTCGC (SEQ ID NO: 1) | CTACGTCCCCGA TCGAAACG (SEQ ID NO: 2) | CGTGGGCGCGGACA GTTGTCGGGAGCG (SEQ ID NO: 3) |
| ASTN1 | CGTAAGCGTTGT TAGCGTAGC (SEQ ID NO: 4) | CGCGAAATCGAA ACGAAAACG (SEQ ID NO: 5) | GTAATTCGTTTGTT TCGTAAGTTGTTCG (SEQ ID NO: 6) |
| DLX1 | TATCGGGATTCG CGTTTGTAC (SEQ IDNO: 7) | CGACCGAACTAA AACTCAACTCG (SEQ ID NO: 8) | CGTAAACGTTAGCT GTTCTGGAAACCG (SEQ ID NO: 9) |

However, the method according to the invention is not limited to these primers for the detection of the methylation status of the regions of genomic DNA. Other primers that amplify/detect other regions of the genomic DNA associated with these genes can be used for detecting the methylation status of these genes. In an embodiment, the quantification of the methylation status of one or more regions of genomic DNA associated with the genes ZNF671, ZNF154, ZNF776, ASTN1, BRINP2, DLX1, METAP1D and/or DLX2 is not compulsory or necessarily critical; however, it is desirable that least one cell with a methylated region can be detected in a background of 1000 cells with the same region of DNA not being methylated.

The present invention is described in detail by the figures and examples below, which are used only for illustration purposes and are not meant to be limiting. Owing to the description and the examples, further embodiments which are likewise included in the invention are accessible to the skilled worker.

FIGURES

EXAMPLES

Figure 1:
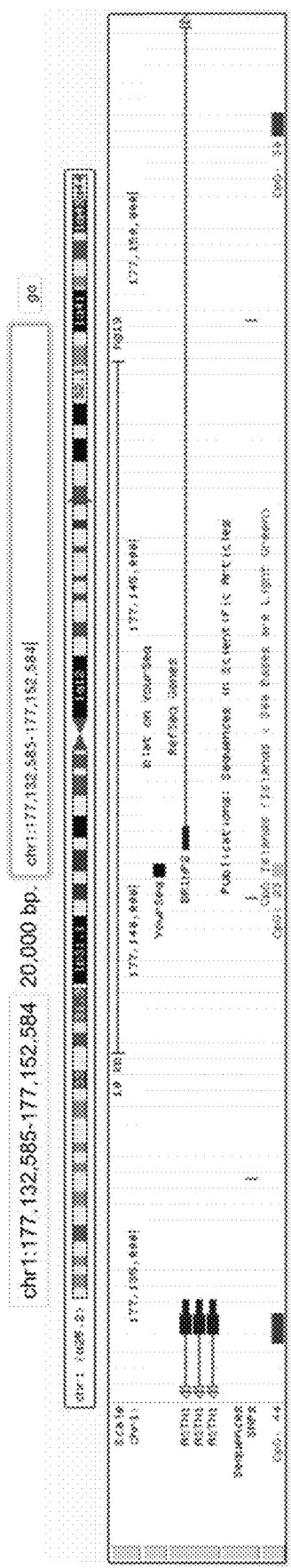
FIG. 1 is a depiction of the genomic DNA associated with the genes ASTN1 and BRINP2 located on chromosome 1.
Figure 2A:
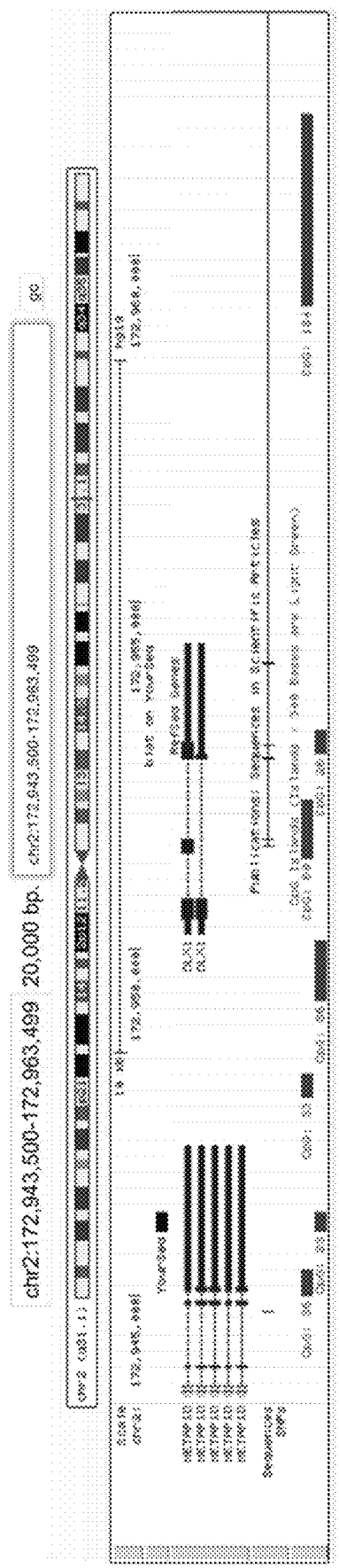
FIGS. 2A and 2B are depictions of the genomic DNA associated with the genes METAP1D, DLX1 and DLX2 located on chromosome 2.
Figure 2B:
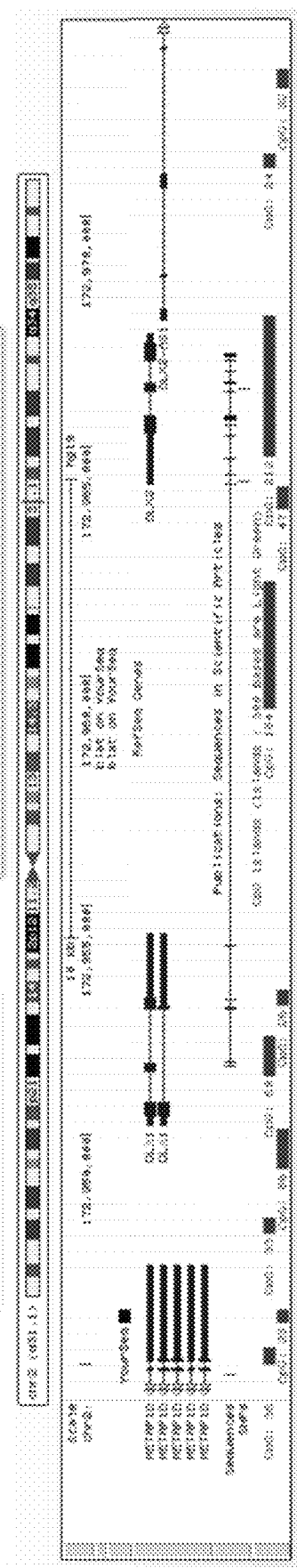
Figure 3:
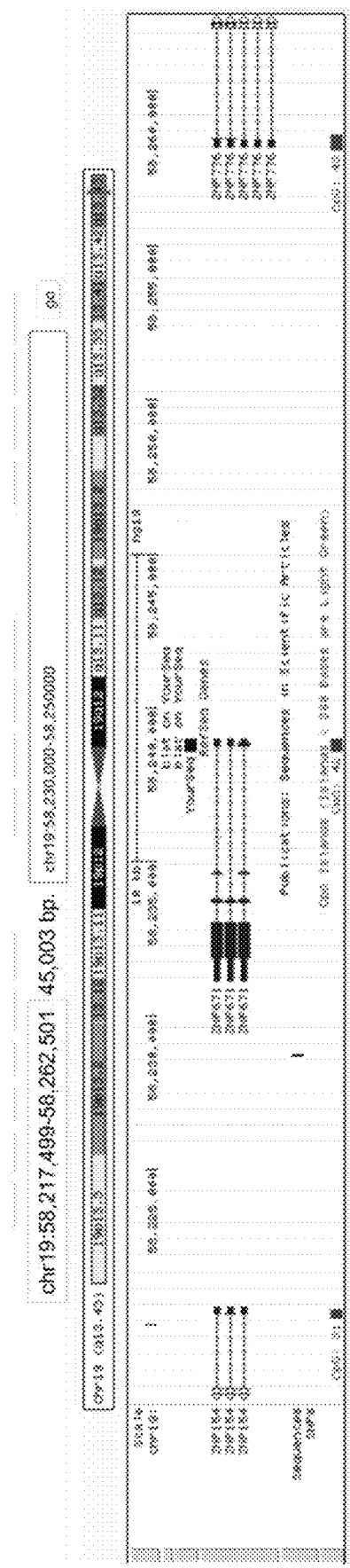
FIG. 3 is a depiction of the genomic DNA associated with the genes ZNF671, ZNF154 and ZNF776 located on chromosome 19.

The techniques and methods used herein are described herein or carried out in a manner known per se and as described, for example, in Green, Sambrook, Molecular Cloning: A Laboratory Manual, 4th Edition (2012) Cold Spring Harbor Laboratory Press, Cold Spring Harbor, N.Y. All methods including the use of kits and reagents are carried out according to the manufacturers' information unless specifically indicated.

Cervical smears were obtained from women and the methylation status of a genomic DNA region (marker region) in the proximity of each of the respective marker genes ZNF671/ZNF154/ZNF776 (referred to as "ZNF671") on chromosome 19, ASTN1/BRINP2 (referred to as "ASTN1") on chromosome 1, and DLX1/METAP1D/DLX2 (referred to as "DLX1") on chromosome 2 was determined. The cervical smears were taken at a time point prior to a histopathological diagnosis of HSIL/CIN3 of the cervical tissue for the patient. In other words, for each of the 30 women from whom cervical smears were taken, at least one cervical smear was taken before a later determination of the presence of severe dysplasia (HSIL/CIN3), and this at least one smear was used to determine the methylation status of the marker genes. Thus, the methylation status of the marker DNA regions was determined in a biological sample containing cervical tissue cells obtained from a patient whose cervical tissue did not show any histopathological indication of neoplasia at that time, and which patient was later diagnosed on the basis of a later-obtained cervical tissue sample to have high-grade dysplasia (HSIL/CIN3) of the cervix.

Cellular pellets from the smear material were obtained and stored at −80° C. prior to testing. DNA was isolated from these cellular pellets using standard DNA isolation routines. As a control for the specificity of the three marker regions, their methylation status also was determined in cervical smear samples (liquid-based cytology samples) from 552 women having shown no histopathological indications of neoplasia (cytology result Pap I).

The isolated DNA was then used for chemical conversion of all non-methylated cytosine residues, using either sodium bisulfite or ammonium bisulfite, followed by purification of the DNA according to standard methods. This chemical conversion is the prerequisite for the discrimination between methylated and non-methylated DNA sequences and thus for the detection of methylated DNA in a background of non-methylated DNA in the genomic regions of interest. This is of prime importance, since the biological sample analyzed usually comprises a mixture of cellular material and the aim of the method is to detect the few methylated DNA molecules originating from the subset of potentially precancerous and cancer cells of the tissue.

The oligonucleotide primers used for analytical PCR were designed to amplify DNA regions of interest from the marker genes that have been previously shown to be methylated in precancerous and cancerous cervical tissue cells. In this example, the below-described primers only allow for the production of an amplification product where the DNA region of interest was methylated. The following PCR primers were used in the analytical PCR:

| Gene | Localization of CpG region in the gene according to Human Genome Assembly Feb. 2009 (GRCh37/hg19) | Primer fwd | Primer rev |
|---|---|---|---|
| ASTN1 | Chr 1: 177,140,121- 177,140,323 | CGTAAGCGTTGT TAGCGTAGC (SEQ ID NO: 4) | CGCGAAATCGAA ACGAAAACG (SEQ ID NO: 5) |
| DLX1 | Chr 2: 172,945,912- 172,946,212 | TATCGGGATTCG CGTTTGTAC (SEQ ID NO: 7) | CGACCGAACTAA AACTCAACTCG (SEQ ID NO: 8) |
| ZNF671 | Chr 19 58,238,586- 58,239,028 | CGGAGGACGTAG TATTTATTCGC (SEQ ID NO: 1) | CTACGTCCCCGA TCGAAACG (SEQ ID NO: 2) |

Figure 4:
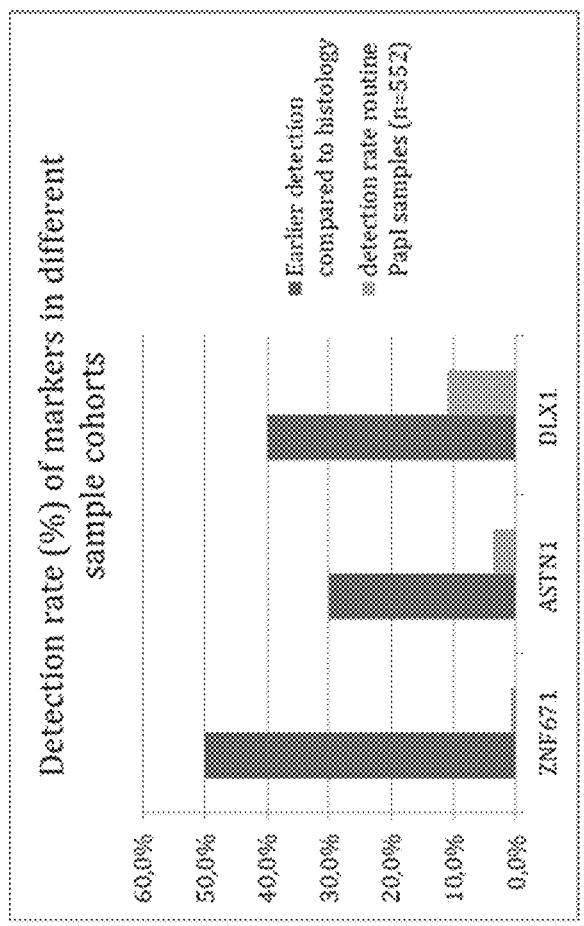
FIG. 4 shows the detection rate (percentage) of methylated markers in cervical smear cells obtained at a time point in patients showing no histopathological/cytomorphological indications of neoplasia in their cervical tissue but who later were diagnosed with a histopathology finding of HSIL/CIN3 for the tissue.

It was observed that PCR products were produced from the three marker regions in samples taken before a HSIL/CIN3 histopathology diagnosis in 9 (30%), 12 (40%), and 15 (50%) of the 30 patients, respectively. See FIG. 4 for a graphical representation of these results. Overall, for 19 (63.3%) of the 30 patients, at least one of the three markers was determined to be methylated in at least one of the samples. In 14 of these 19 patients at least two markers, and in 7 of these 14 patients, all three markers were methylated.

Moreover, the three marker regions were determined to be methylated in samples taken 3-31, 3-75, and 3-30 months before a separate later taken sample showed HSIL/CIN3 histopathology, respectively. In contrast, the same three marker regions were detectable in only 20 (3.6%), 61 (11.1%), and 5 (0.9%) of the 552 control samples from women with a cytology finding of Pap I, respectively.

Table 1 sets forth the time interval between the time the cervical smear was taken, where no signs of dysplasia/neoplasia were detected but one of the marker genes was methylated, and the time at which another sample was taken from the patient showing a HSIL/CIN3 dysplasia.

TABLE 1

| Time interval | ASTN1 | DLX1 | ZNF671 |
|---|---|---|---|
| 3-6 months | 2/9 (22.2%) | 4/12 (33.3%) | 7/15 (46.7%) |
| 7-12 months | 3/9 (33.3%) | 4/12 (33.3%) | 2/15 (13.3%) |
| 13-24 months | 2/9 (22.2%) | 2/12 (16.7%) | 2/15 (13.3%) |
| >24 months | 2/9 (22.2%) | 2/15 (16.7%) | 4/15 (26.7%) |

Table 2 sets forth the percentage of the 30 patients tested that developed a HSIL/CIN3 dysplasia in terms of months after the smear that was tested was obtained, i.e., the percentage of patients for whom an early detection of a HSIL/CIN3 dysplasia was effected by the determination of the methylation status of each of the marker genes.

TABLE 2

| Time in months | ASTN1 | DLX1 | ZNF671 |
| --- | --- | --- | --- |
| 3-6 | 6.7% | 13.3% | 23.3% |
| 7-12 | 10.0% | 13.3% | 6.7% |
| 13-24 | 6.7% | 6.7% | 6.7% |
| >24 | 6.7% | 6.7% | 13.3% |
| No early detection | 70.0% | 60.0% | 50.0% |

Altogether these results demonstrate that the determination of the methylation status of a genomic DNA sequence associated with at least one of the marker genes ZNF671, ZNF154, ZNF776, ASTN1, BRINP2, DLX1, METAP1D and/or DLX2 in a sample obtained from a patient provides a useful tool for early determination of an increased risk for developing a high-grade cervical lesion (HSIL/CIN3) that has a significant potential to progress to cancer. It becomes clear from these results that the methylation status of these three genes allows for a timely assessment of the risk to develop a high-grade intraepithelial lesion, especially a CIN3. The fact that the genomic DNA sequences associated with these marker genes are only infrequently methylated in samples from patients with normal cytology (Pap I) underscores the high diagnostic value of a test based on the methylation status of one or more regions of genomic DNA associated with the marker genes ZNF671, ZNF154, ZNF776, ASTN1, BRINP2, DLX1, METAP1D and/or DLX2.

We claim:

1. A method for determining the risk for developing neoplasia in cervical, vaginal, urethral, or anogenital tissue of a human patient which cervical, vaginal, urethral, or anogenital tissue, respectively, shows no histopathological indication of neoplasia, the method comprising:
 (a) determining the methylation status of one or more regions of genomic DNA associated with the gene ZNF671 in a biological sample containing cells of the cervical, vaginal, urethral, or anogenital tissue, respectively, obtained from the patient, wherein the one or more regions of genomic DNA associated with the gene ZNF671 can be detected with an oligonucleotide probe having the nucleic acid sequence of SEQ ID NO: 3 and wherein the one or more regions of genomic DNA associated with the gene ZNF671 comprises a region of genomic DNA that can be amplified by a primer pair comprising a first primer having the nucleic acid sequence of SEQ ID NO: 1 and a second primer having the nucleic acid sequence of SEQ ID NO: 2, and wherein when the one or more regions is methylated in the biological sample, the patient has an increased risk for developing neoplasia in the tissue compared to a human patient in which the regions are not methylated; and
 (b) administering to the patient having an increased risk for developing neoplasia in the cervical, vaginal, urethral, or anogenital tissue, respectively, a medicament to reduce risk of neoplasia in the tissue.

2. The method according to claim 1, wherein the methylation status of the promoter region of the gene ZNF671 is determined.

3. The method according to claim 1, wherein the methylation status is determined by comparing the amount of methylation in the biological sample to the amount of methylation determined in a control sample.

4. The method according to claim 1, wherein the neoplasia is intraepithelial neoplasia.

5. The method according to claim 1, wherein the cervical neoplasia is HSIL/CIN3 cervical neoplasia or cervical cancer.

6. The method according to claim 1, wherein the biological sample is a cervical or rectal smear.

7. The method according to claim 1, wherein the histopathological state of the tissue is determined colposcopically.

8. The method according to claim 1, wherein the biological sample obtained from the patient is used to determine the methylation status of the one or more regions of genomic DNA associated with the gene ZNF671 and to determine the histopathological state of the tissue.

9. The method according to claim 1, wherein the biological sample obtained from the patient used to determine the methylation status of the one or more regions of genomic DNA associated with the gene ZNF671 is a different biological sample obtained from the patient than the biological sample used to determine the histopathological state of the tissue.

10. The method according to claim 1, wherein the biological sample obtained from the patient used to determine the methylation status is obtained after the histopathological state of the tissue has been determined.

11. The method according to claim 1, wherein the patient is infected with papillomavirus.

12. The method according to claim 1, wherein the patient is free of papillomavirus infection.

13. The method according to claim 1, wherein the methylation status is determined by nanopore sequencing.

14. The method according to claim 1, wherein the methylation status is determined by methylation-specific PCR (MSP).

15. The method according to claim 14, wherein the MSP is a quantitative MSP (QMSP).

16. The method according to claim 14, wherein the MSP is performed using the primer pair comprising a first primer having the nucleic acid sequence of SEQ ID NO: 1 and a second primer having the nucleic acid sequence of SEQ ID NO: 2.

17. The method according to claim 14, wherein the MSP is quantitative MSP (QMSP) and the QMSP is based on the use of fluorescent probes.

18. The method according to claim 1, wherein after the tissue has been determined to have an increased risk for developing neoplasia, the method further comprises determining the histopathological state of the tissue.

19. The method according to claim 18, wherein the further determining occurs within 3 months, 6 months, 9 months, or 12 months of the determination of an increased risk for developing neoplasia.

20. The method according to claim 1, the method further comprising determining the methylation status of one or more regions of genomic DNA associated with the genes ZNF154, ZNF776, ASTN1, BRINP2, DLX1, METAP1D and/or DLX2.

21. The method according to claim 1, wherein the medicament is an anti-inflammatory agent or a methylation inhibitor.

22. The method according to claim 1, wherein the medicament is azacytidine or decitabine.

23. The method according to claim 1, wherein the tissue is cervical tissue.

24. A method for selecting a human patient showing no histopathological indication of neoplasia in cervical, vaginal, urethral, or anogenital tissue to undergo more frequent screening for neoplasia in the cervical, vaginal, urethral, or anogenital tissue, respectively, the method comprising:
(a) selecting a human patient in which one or more regions of genomic DNA associated with the gene ZNF671 is methylated in a biological sample containing cells of the cervical, vaginal, urethral, or anogenital tissue, respectively, obtained from the patient, wherein the one or more regions of genomic DNA associated with the gene ZNF671 can be detected with an oligonucleotide probe having the nucleic acid sequence of SEQ ID NO: 3 and wherein the one or more regions of genomic DNA associated with the gene ZNF671 comprises a region of genomic DNA that can be amplified by a primer pair comprising a first primer having the nucleic acid sequence of SEQ ID NO: 1 and a second primer having the nucleic acid sequence of SEQ ID NO: 2, and
(b) screening the patient selected in (a) for neoplasia in cervical, vaginal, urethral, or anogenital tissue, respectively, every 12 months.

25. The method according to claim 24, wherein the more frequent screening is histopathology-based screening.

26. The method according to claim 24, where the more frequent screening is every 6 months or every 3 months.

27. The method according to claim 24, the method further comprising determining the methylation status of one or more regions of genomic DNA associated with the genes ZNF154, ZNF776, ASTN1, BRINP2, DLX1, METAP1D and/or DLX2.

28. The method according to claim 24, wherein the tissue is cervical tissue.

29. A method for reducing risk of neoplasia in a tissue of a human patient, which patient has an increased risk for developing neoplasia in the tissue, said method comprising:
(a) determining the risk for developing neoplasia in cervical, vaginal, urethral, or anogenital tissue showing no histopathological indication of neoplasia by (i) determining the histopathological state of cervical, vaginal, urethral, or anogenital tissue of a human patient; and (ii) determining the methylation status of one or more regions of genomic DNA associated with the gene ZNF671 in a biological sample containing cells of the cervical, vaginal, urethral, or anogenital tissue, respectively, obtained from the patient before or after step (i), wherein the one or more regions of genomic DNA associated with the gene ZNF671 can be detected with an oligonucleotide probe having the nucleic acid sequence of SEQ ID NO: 3 and wherein the one or more regions of genomic DNA associated with the gene ZNF671 comprises a region of genomic DNA that can be amplified by a primer pair comprising a first primer having the nucleic acid sequence of SEQ ID NO: 1 and a second primer having the nucleic acid sequence of SEQ ID NO: 2, and wherein when the histopathological state of the tissue indicates an absence of neoplasia, and when the one or more regions is methylated in the biological sample, the patient has an increased risk for developing neoplasia in the tissue, and
(b) administering to the patient having an increased risk for developing neoplasia as determined in step (a) a medicament to reduce risk of neoplasia in the tissue.

30. The method according to claim 29, the method further comprising determining the methylation status of one or more regions of genomic DNA associated with the genes ZNF154, ZNF776, ASTN1, BRINP2, DLX1, METAP1D and/or DLX2.

31. The method according to claim 29, wherein the medicament is an anti-inflammatory agent or a methylation inhibitor.

32. The method according to claim 29, wherein the medicament is azacytidine or decitabine.

33. The method according to claim 29, wherein the tissue is cervical tissue.

* * * * *